United States Patent [19]
Jozwiak

[11] Patent Number: 5,837,151
[45] Date of Patent: Nov. 17, 1998

[54] METHODS FOR SEPARATING SOIL FROM SOIL LADEN WATER IN DISHWASHERS

[75] Inventor: Todd M. Jozwiak, Benton Harbor, Mich.

[73] Assignee: Whirlpool Corporation, Benton Harbor, Mich.

[21] Appl. No.: 848,615

[22] Filed: Apr. 29, 1997

Related U.S. Application Data

[60] Provisional application No. 60/005,365 Oct. 17, 1995.

Related U.S. Application Data

[62] Division of Ser. No. 713,488, Sep. 13, 1996, Pat. No. 5,770,058.

[51] Int. Cl.[6] .............................. B08B 3/02; B01D 21/26
[52] U.S. Cl. ....................... 210/787; 210/740; 210/800; 210/806; 134/25.2; 134/37
[58] Field of Search .............................. 241/24.1, 24.11, 241/24.16; 134/25.2, 33; 210/787, 790, 800, 806, 173; 494/37

[56] References Cited

U.S. PATENT DOCUMENTS

| | | |
|---|---|---|
| 1,583,236 | 5/1926 | Murrish . |
| 3,322,285 | 5/1967 | Lopp . |
| 3,575,185 | 4/1971 | Barrbulesco . |
| 3,669,132 | 6/1972 | Mamrose . |
| 3,989,054 | 11/1976 | Mercer . |
| 4,038,103 | 7/1977 | Grunewald . |
| 4,039,452 | 8/1977 | Fernandez . |
| 4,150,679 | 4/1979 | Cushing et al. . |
| 4,297,210 | 10/1981 | Delfosse . |
| 4,319,599 | 3/1982 | Dingler et al. . |
| 4,346,723 | 8/1982 | Geiger . |
| 4,347,861 | 9/1982 | Clearman et al. . |
| 4,392,891 | 7/1983 | Meyers . |
| 4,559,959 | 12/1985 | Meyers . |
| 4,673,441 | 6/1987 | Mayers . |
| 4,971,518 | 11/1990 | Florin . |
| 4,972,861 | 11/1990 | Milocco et al. . |
| 5,097,855 | 3/1992 | Martinsson et al. . |
| 5,165,433 | 11/1992 | Meyers . |
| 5,333,631 | 8/1994 | Kirkland et al. . |
| 5,345,957 | 9/1994 | Cooper et al. . |

FOREIGN PATENT DOCUMENTS 1352655  5/1974  United Kingdom .

*Primary Examiner*—David A. Reifsnyder
*Attorney, Agent, or Firm*—Hill & Simpson

[57] ABSTRACT

A centrifugal soil separator for a dishwasher having a rotating centrifuge connected for rotation with a centrifugal impeller, the centrifugal impeller providing a majority of recirculating wash water for the dishwasher while the centrifuge accepts a second portion of flow and spins that portion of flow for soil separation and to achieve a pumping action to move that quantity of water to the wash water delivery system with the quantity of water moved by the centrifugal impeller. By a coordinated stopping, reversing and starting action of the centrifuge, soil collected therein can be disposed to a soil sizing and drain apparatus for flushing and draining the centrifuge.

12 Claims, 3 Drawing Sheets

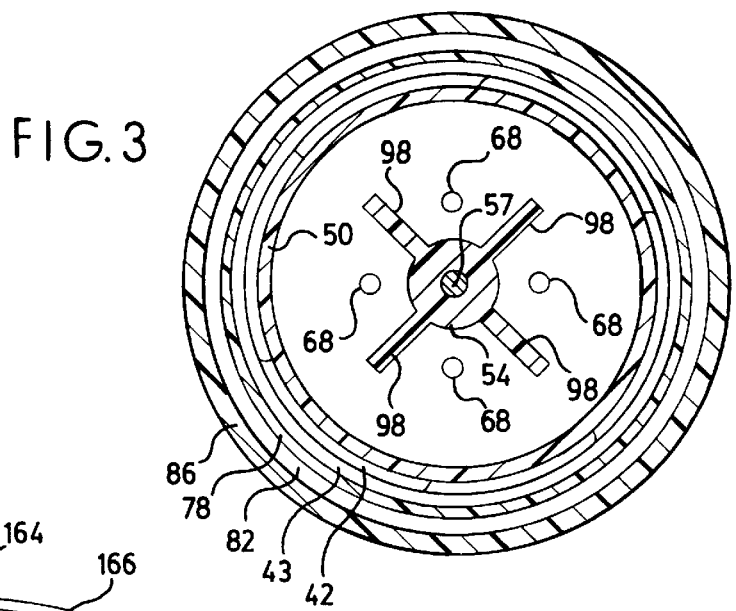
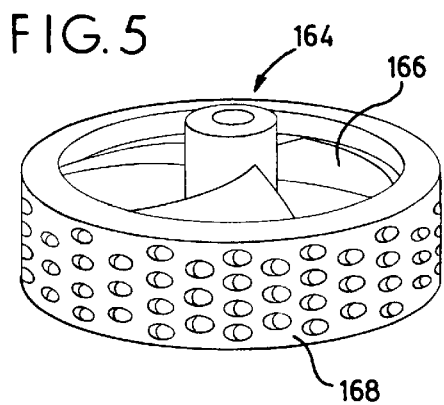
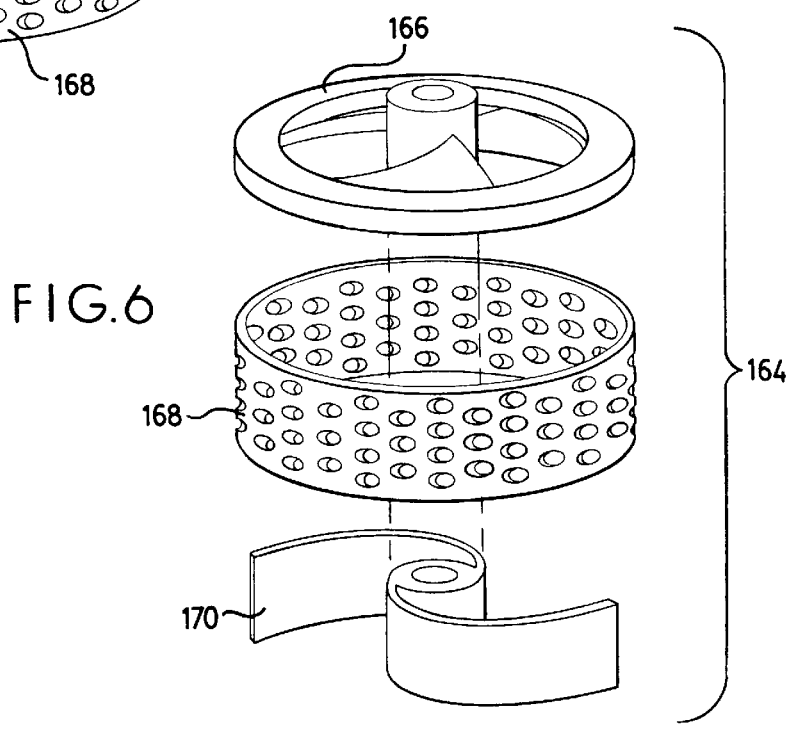

METHODS FOR SEPARATING SOIL FROM SOIL LADEN WATER IN DISHWASHERS

This is a division of application Ser. No. 08/713,488, filed Sep. 13, 1996, now allowed, U.S. Pat. No. 5,770,058, and claims the benefit of U.S. Provisional Application No.: 60/005,365 filed Oct. 17, 1995.

BACKGROUND OF THE INVENTION

The invention relates to dishwashers, in particular to food soil separation and disposal mechanisms.

Many commercially available dishwashers utilize centrifugal forces generated by the dishwasher pump to provide for soil separation, and further rely on settling chambers or filters to contain the soils. U.S. Pat. No. 5,165,433 for example discloses such a system.

In that patent, an accumulator annular wall is provided around an annular pump chamber wall. Water is permitted to flow over the pump chamber wall into an annular slot area defined between the walls. An orifice through the accumulator wall allows water and soil to exit this annular slot area into an accumulator or settling area. A screen covering that area allows water to exit upwardly into the dishwasher area while soil is retained in the sump area to be disposed at timed intervals.

Such systems have the drawbacks of keeping filters free flowing or preventing disturbances in settling areas. To solve those problems, typically extra water is required in the form of back flush nozzles or large volume settling tanks. It is advantageous however to reduce water consumption and thereby conserve energy.

SUMMARY OF THE INVENTION

It is an object of the present invention to reduce energy and water consumption or storage in a dishwasher soil separation and disposal system. It is an object of the present invention to provide a soil separation system which does not require fine filtering elements or large settling tanks. It is an object of the present invention to provide a soil separation and disposal system which prevents accumulation of particles on dishes during a wash cycle. It is an object to provide a system which does not require water flow to back flush filters or screens.

The objects of the invention are achieved in that a centrifugal separator is provided which separates and contains soil particles without the need for a settling tank or fine filtering screens. The system also provides soil "sizing" (grinding or size reduction) and a drain system. A pump housing provides a coarse particle screen, flow gathering and redirection channels and additional soil separation means.

The centrifugal separator functions on the principle that a spinning column of water with different diameters at each end will pump water axially. Such a spinning column will also be acted upon by centrifugal forces. As soiled water is pumped through the separator, the centrifugal forces separate food soils based on their densities. Heavier than water soils collect on the outer wall and lighter than water soils collect in the center. By properly controlling the exit, "clean" water can be allowed to escape leaving the soils trapped.

To dispose trapped soils, the spinning column of water is stopped. Some of the "heavy" food soils are allowed to fall out of the column at this time. By reversing the spinning direction and activating the drain system, the water will be pumped out of the dishwasher. Due to the shape of the centrifuge, a significant amount of water and possible food soils are still contained and suspended in the separator after the unit has been pumped dry. By again stopping the motor, the remaining water and soils will fall out of the system below the inlet of the separator. At this point, the pump is again spun in the drain direction to complete the system draining.

Alternatively, disposing of water and food soils may be achieved by either stopping or agitating the separator while allowing a second, smaller pump to draw the soil and water from the unit.

Stopping and starting the system presents a disadvantage in that the system attempts to pump at a high rate during start up. With a large exit opening, this high rate can empty much of the soil that was trapped and dispose it on the dish load or plug spray arm nozzles. To correct this problem, a ring of holes on the centrifuge exit are used in place of an open hole or band. By controlling the number and size of the holes, both the flow rate and soil particle size can be regulated during start-up and normal operation.

Attached to the separator is a centrifugal impeller. Because the separator is designed to pump at a relatively low flow rate, a centrifugal impeller serves to provide the main pumping action for the dishwasher. The impeller draws its water through a coarse mesh screen which prevents large food soils from plugging the water delivery system. This coarse mesh may be configured in many different ways to allow either automatic or manual cleaning.

The impeller can also aid soil separation by adding a soil concentration wall similar to that used in U.S. Pat. 5,165,433. This wall allows soil concentrations to be increased and fed to the separator for containment and eventual disposal.

Both the water from the impeller and the separator converge at the outer upper edge of the separator. Here, the spinning water is gathered and redirected by a diffuser to supply the water feed system to the water delivery arms within the dish compartment.

BRIEF DESCRIPTION OF THE DRAWINGS

FIG. 3 is a sectional view taken generally along line III—III of FIG. 2;

FIG. 5 is a perspective view of the sizing mechanism shown in FIG. 4; and

FIG. 6 is an exploded perspective view of the mechanism of FIG. 5.

DETAILED DESCRIPTION OF THE PREFERRED EMBODIMENTS

Figure 1:
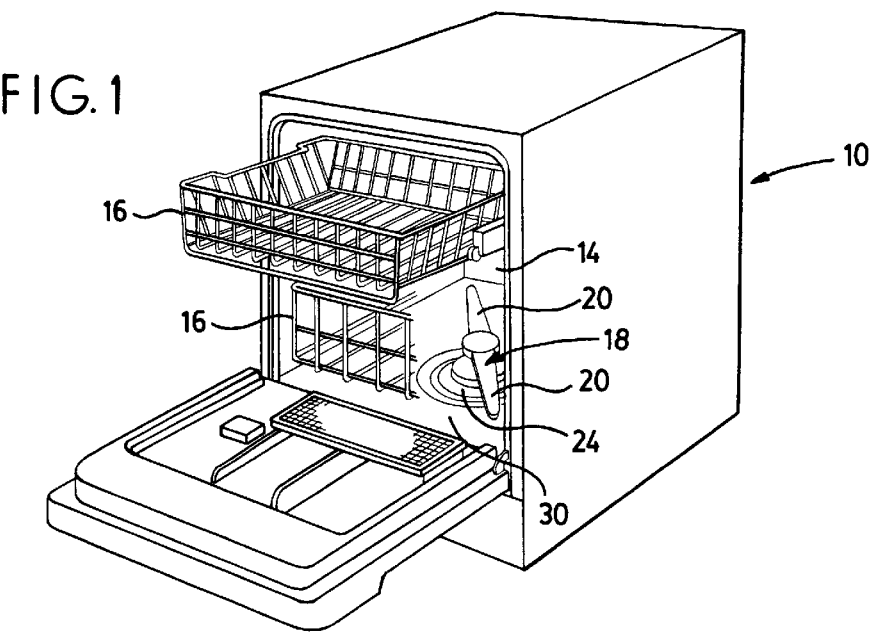
FIG. 1 is a perspective view of a dishwasher using the soil separating system of the present invention.

FIG. 1 illustrates a dishwasher 10 having a dish compartment 14 and holding racks 16 for holding dishes, as is known. At a bottom of the dish compartment 14 is a rotary water delivery mechanism 18 including water wash arms 20. The delivery mechanism 18 is mounted on top of a soil separator 24 via a water conduit 26 which feeds water to the delivery mechanism 18 (shown in FIG. 2). An upper wash arm can also be provided and flow connected to the separator 24 (not shown).

Figure 2:
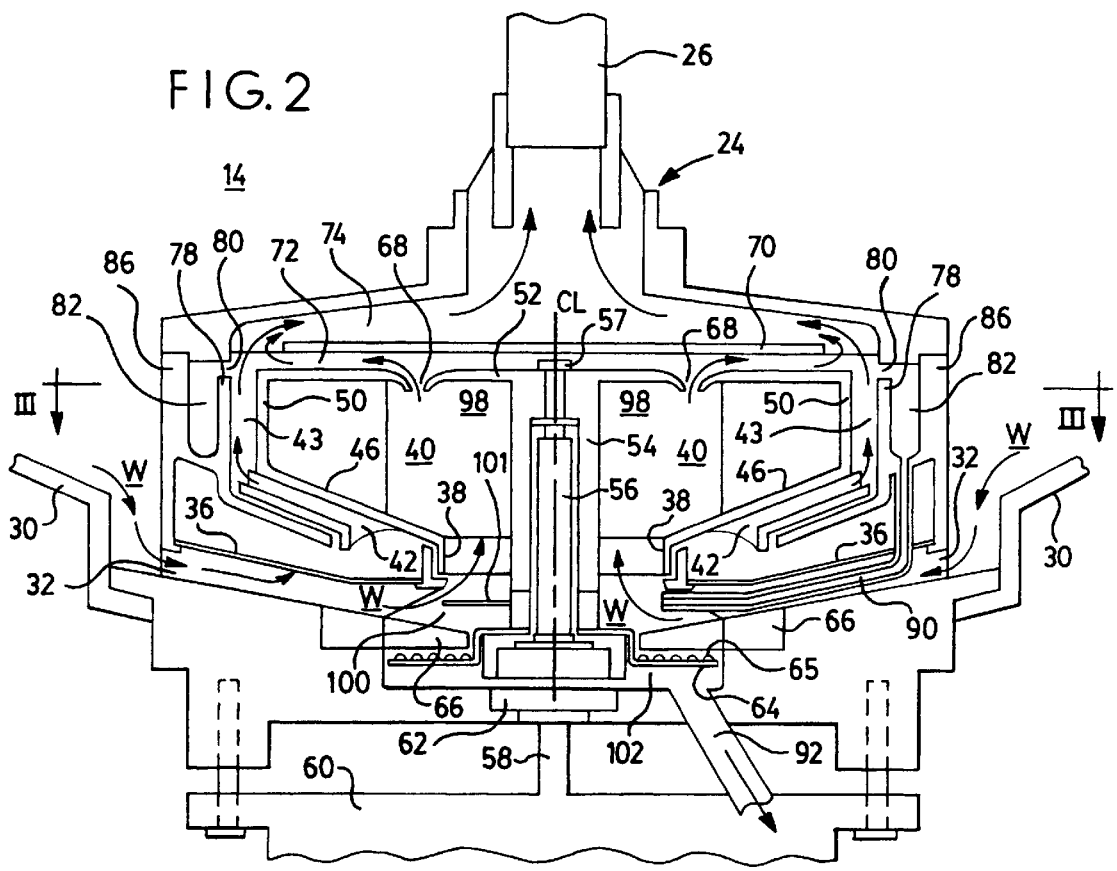
FIG. 2 is a longitudinal sectional view of the soil separator mechanism of FIG. 1.

FIG. 2 shows the soil separator 24 in more detail. The separator 24 is mounted on a floor 30 of the dish compartment 14. Soil laden water W proceeds through an annular gap 32 into the separator 24. A coarse screen 36 is provided in annular form around a center line of the separator 24. Water may proceed through the coarse screen 36 of a first flow rate and also proceed radially inwardly past the screen 36 to a central opening 38 to be drawn into the centrifuge 40 at a second flow rate. Soil laden water W passing through the screen 36 is pumped by centrifugal impeller 42 upwardly as shown.

The impeller 42 is mounted to an inclined annular wall 46 partially defining the centrifuge 40. Inclined annular wall 46 continues to an annular vertical wall 50 which is closed by a disk shaped top wall 52. The disk shaped top wall 52 provides a central hub 54 which is connected by a shaft 56 and screw or bolt 57 to a motor shaft 58 driven by a motor 60. A seal 62 is provided to prevent water within the separator 24 from dripping down onto, for example, the motor or paneling beneath the dishwasher compartment 14. A sizing rotor 64 and/or chopping blade 101 is provided attached to the shaft 56 for rotation therewith. The sizing rotor 64 provides cutting or grating elements 65 which as rotated, grind food particles against stationary vanes 66. The chopping blade 101 provides high velocity impacts on soil to reduce particle size. Reduced size particles from either device proceed out of the drain 92, if operated in a "drain" mode, or allowed to remain in areas 100 and 102 if operated in a "wash" mode, until the system is drained.

Through the disk shaped top wall 52 are arranged a plurality of holes 68 shown coined downwardly which allow water spun within the centrifuge 40 to pass upwardly out of the centrifuge 40. A water distribution diffuser 70 is provided above the hole 68. A passage 72 defined by the top wall 52 and diffuser 70 allows the water to join with the water moved upwardly by the centrifugal impeller 42 and proceed into a plenum 74 flow connected to the pipe 26 for distribution to the water distribution mechanism 18 for spraying the dishes.

The mechanism 18 in all other respects is similar to known dishwasher wash arms. Additionally, if a top mounted upper washer arm is used, a conduit can be employed to flow connect the plenum 74 to a hose leading to the upper wash arm (not shown).

Also, an annular soil concentration wall 78 can be provided surrounding the vertical annular wall 50. Water moved by the centrifugal impeller 42 and influenced by the spinning vertical annular wall 50 allows entrained soil to pass through an annular gap 80 into an annular sump 82 defined between the wall 78 and an outer wall 86 of the mechanism 24. A sump drain line 90 is provided leading from the sump 82 down to the area of the opening 38. Soil accumulated in the sump 82 can be therefore transported down to the separator entrance 38 for collection and confinement.

The centrifugal impeller 42 pumps water through an annular vertical channel 43 upward to supply the pipe 26 with wash water.

As shown in FIG. 3, the centrifuge 40 is shown with radially aligned paddles 98 extending from the hub 54 for imparting rotational force to the column of water held within centrifuge 40. The holes 68 are shown which allow the central portion of the water within the centrifuge 40 to leave the centrifuge to pass through the pipe 26 to the recirculated into the dish compartment 14. The size and radial location of the holes 68 can be controlled to further screen soil particles.

In operation, the centrifuge 40 functions on the principle that a spinning column of water with different diameters at each end will pump water. The centrifuge 40 has a smaller diameter at its entrance 38, and a slightly larger diameter defining the location of holes 68. Thus when the motor shaft 58 spins, the connector shaft 56 spins which spins the hub 54. The hub 54 spins the centrifuge walls 52, 50, 46 and the paddles 98 to spin water held within the centrifuge 40. Centrifugal forces separate food soils based on their densities within the centrifuge 40. Heavier than water soils collect on the outer wall of the centrifuge and lighter than water soils collect in the center. By locating the holes 68 at a preselected radial distance from a center line CL of the centrifuge at least equal to radial location of inlet wall 38 to the same centerline CL, relatively clean water can be dispensed out of the holes 68.

To dispose the trapped soils, periodically, the centrifuge 40 is stopped. Some of the heavy food soils may fall out of the centrifuge 40 at this time. By activating the drain system and either allowing the centrifuge 40 to remain stationary, agitate by repeated direction changes, or rotate continuously in either direction, the water and soil will be pumped out of the dishwasher. Whether or not the centrifuge 40 is rotating or in which direction is dependent on the configuration of the soil sizing mechanisms and the type of food soils expected to be handled. In the case of a rotating centrifuge, some food particles and water will remain within the centrifuge after the unit has been pumped dry. At this point in operation, the centrifuge 40 is again stopped and the remaining water and soil should flow downwardly out of the centrifuge down to the sizing and drain area 100. The drain system is again activated to complete the system draining.

The centrifuge 40 is designed to pump water out of the holes 68 at a relatively low flow rate. The centrifugal impeller 42 on the other hand serves to provide a main pumping action for the dishwasher. The impeller 42 draws water across the screen 36 for coarse screening.

Figure 4:
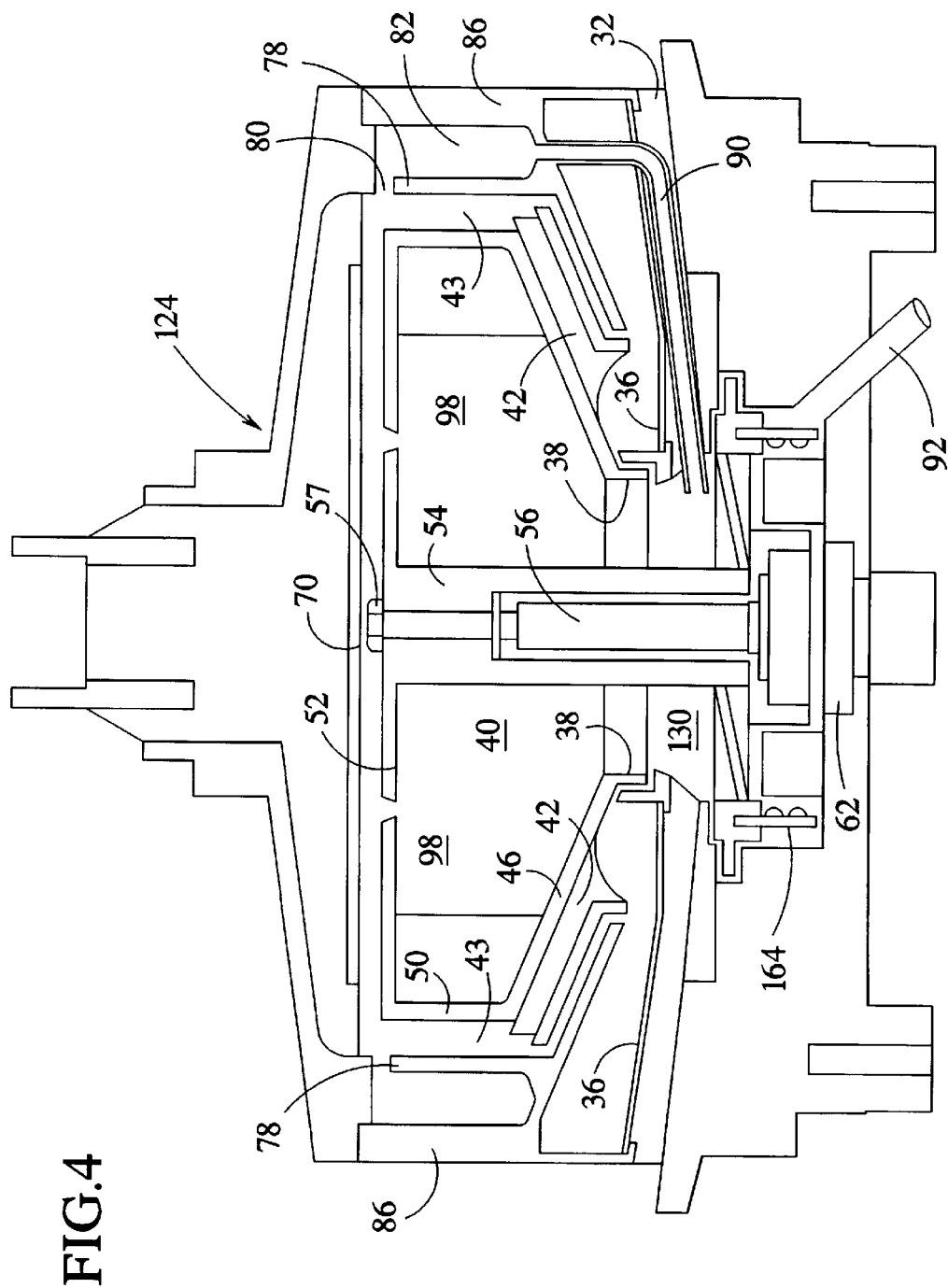
FIG. 4 is a longitudinal sectional view of an alternate embodiment of the separator of FIG. 2.

FIG. 4 describes an alternate embodiment separator 124 having a different soil sizing and drain area 130 including an alternate soil sizing rotor 164. This rotor 164 is shown in detail in FIGS. 5 and 6.

The rotor 164 includes a propeller 166 which when spun in a draining direction encourages flow through the rotor 164 and when spun in a reverse direction (wash direction) prevents flow through the rotor 164. A perforated cylinder 168 is fastened to the propeller 166. The cylinder 168 allows water to pass through to drain during a drain cycle. The cylinder will also chop and size food particles. A spring finger element 170 passes an inside of the cylinder 168 to assist in forcing food particles against the cylinder inside surface to effectively grate or grind the particles. The finger elements 170 can be designed to deflect or rotate to prevent stalling the motor if a large hard particle wedges between the finger and the cylinder 168.

Although the present invention has been described with reference to a specific embodiment, those of skill in the art will recognize that changes may be made thereto without departing from the scope and spirit of the invention as set forth in the appended claims.

The embodiments of the invention in which an exclusive property or privilege is claimed are defined as follows:

1. A method for separating soil from soil laden water for a recirculating wash water dishwasher; comprising the steps of:

providing a soil separator including a centrifuge;

receiving wash water from a dish compartment of said dishwasher into said soil separator;

in said soil separator receiving a first flow of said wash water into said centrifuge;

spinning said centrifuge with a motor to maintain a spinning column of water having a vertically upwardly increasing diameter;

pumping water through said centrifuge by said spinning of said centrifuge to an exit located at a top region of said centrifuge;

reapplying water exiting said centrifuge to said dish compartment; and draining at least some of the soil from the soil separator.

2. The method according to claim 1 comprising the further steps of:

receiving a second flow of said wash water and passing said second flow through a coarse screening, and pumping said second flow to combine with said first flow delivered by said centrifuge and passing both said first and second flows to said dish compartment.

3. The method according to claim 2 further comprising the step of flowing at least some of the second flow of the wash water into said soil separator after the step of passing said second flow through the course screening.

4. The method according to claim 1 comprising the further step of periodically stopping said centrifuge to allow soil and water to flow by gravity downwardly to be drained from the separator; and restarting the centrifuge in a reverse direction from a first direction in said spinning said centrifuge step to assist in draining of said centrifuge of soil water.

5. The method according to claim 4 comprising the further steps of after restarting said centrifuge in the reverse direction, stopping said centrifuge to allow soil and water to flow by gravity downwardly to be drained; and restarting the centrifuge again in the reverse direction to drain said water from said centrifuge.

6. The method according to claim 4 comprising the further step of, while draining, sizing said soil to be drain with a rotating sizing mechanism.

7. The method according to claim 1 wherein the step of spinning said centrifuge further comprises the step of separating soil heavier than water and soil lighter than water in said wash water into separate areas in the spinning column of water.

8. The method according to claim 1 wherein the step of pumping water through said centrifuge further comprises the step of pumping water from generally a mid-area of the spinning column of water between radially innermost and outermost areas of the spinning column of water.

9. The method according to claim 1 wherein the step of draining at least some of the soil from the soil separator comprises a step selected from the group consisting of stopping the spinning of the centrifuge, repeatedly changing a direction of spin of the centrifuge, continuing to spin the centrifuge, reversing a direction of spin of the centrifuge, and combinations thereof.

10. A method of washing soiled dishes in a dishwasher comprising the steps of:

applying water to the soiled dishes;

removing at least some soil from the dishes with the water to form soiled water;

rotating the soiled water in a column having different diameters at opposite ends of the column;

moving at least some of the soil in the rotating column of soiled water to form column areas having a relatively high concentration of soil and a relatively low concentration of soil;

screening soil from a portion of the soiled water to form screened soiled water; and combining the screened soiled water with the water from the column area having a relatively low concentration of soil to form soil reduced water; and wherein the step of applying water to the soiled dishes comprises the step of applying the soil reduced water to the dishes.

11. A method of recirculating water in a dishwasher comprising the steps of:

distributing the water in a dish compartment of the dishwasher;

flowing the water from the dish compartment to a soil separator;

spinning the soil separator by driving the soil separator with a motor;

spinning the water in the soil separator to form a column of water having different diameters at opposite ends of the column of water; and flowing the water from the column of water to the dish compartment.

12. The method of claim 11 further comprising the steps of:

bypassing a portion of the water from the dish compartment around the spinning column of water; and flowing the portion of water bypassing the spinning column of water to the dish compartment.

* * * * *